United States Patent
Mori et al.

(10) Patent No.: US 7,630,754 B2
(45) Date of Patent: Dec. 8, 2009

(54) INTRA-SUBJECT DEVICE AND RELATED MEDICAL DEVICE

(75) Inventors: Takeshi Mori, Tokyo (JP); Takemitsu Honda, Tokyo (JP); Masatoshi Homan, Tokyo (JP)

(73) Assignee: Olympus Corporation, Tokyo (JP)

( * ) Notice: Subject to any disclaimer, the term of this patent is extended or adjusted under 35 U.S.C. 154(b) by 479 days.

(21) Appl. No.: 11/176,860

(22) Filed: Jul. 7, 2005

(65) Prior Publication Data
US 2006/0020214 A1 Jan. 26, 2006

(30) Foreign Application Priority Data
Jul. 7, 2004 (JP) ............... 2004-200580

(51) Int. Cl.
*A61B 5/06* (2006.01)
*H04N 9/64* (2006.01)
(52) U.S. Cl. ...................... 600/476; 348/243
(58) Field of Classification Search ................. 600/478, 600/476, 407, 427, 160; 348/76, 248, 243; 345/213
See application file for complete search history.

(56) References Cited

U.S. PATENT DOCUMENTS

| | | | |
|---|---|---|---|
| 5,604,531 A | 2/1997 | Iddan et al. | |
| 5,926,214 A * | 7/1999 | Denyer et al. | 348/241 |
| 6,061,092 A * | 5/2000 | Bakhle et al. | 348/243 |
| 6,738,528 B1 * | 5/2004 | Nio et al. | 382/268 |
| 7,161,626 B1 * | 1/2007 | Nara | 348/243 |
| 2001/0035902 A1 | 11/2001 | Iddan et al. | |
| 2002/0158976 A1 * | 10/2002 | Vni et al. | 348/243 |
| 2005/0099515 A1 | 5/2005 | Tsuruoka | |
| 2005/0288595 A1 * | 12/2005 | Bettesh | 600/478 |

FOREIGN PATENT DOCUMENTS

| | | |
|---|---|---|
| JP | 2002-345743 | 12/2002 |
| WO | WO 2004/019608 A1 | 3/2004 |
| WO | WO 2004/049947 A2 | 6/2004 |

* cited by examiner

*Primary Examiner*—Eric F Winakur
*Assistant Examiner*—Lawrence N Laryea
(74) *Attorney, Agent, or Firm*—Scully, Scott, Murphy & Presser, P.C.

(57) ABSTRACT

An intra-subject device is introduced into a subject to acquire information of the interior of the subject and has a lighting member to output an illuminating light for illuminating the interior of the subject and an imaging member to acquire an image of the interior of the subject. The intra-subject device also has a parameter memory to store a parameter for canceling a noise contained in color information of the image. The intra-subject device also has a radio-transmitting section that radio-transmits the image information, to which the parameter stored in the parameter memory is added.

9 Claims, 7 Drawing Sheets

INTRA-SUBJECT DEVICE AND RELATED MEDICAL DEVICE

CROSS-REFERENCE TO RELATED APPLICATION

This application is based upon and claims the benefit of priority from prior Japanese Patent Application No. 2004-200580, filed on Jul. 7, 2004, the entire contents of which is incorporated herein by reference.

BACKGROUND OF THE INVENTION

1. Field of the Invention

The present invention relates to an intra-subject device loaded within the interior of a subject and a medical device including the intra-subject device, an example of which is a capsule type endoscope. More particularly, the present invention relates to a technology of canceling noise contained in image information, when the image information is radio-transmitted from the intra-subject device or the related medical device thereof.

2. Description of the Related Art

Recently, in the field of the endoscopies, a capsule type endoscope having an imaging function and a radio-communication function has come into practice. The capsule type endoscope, during the time for observation after being swallowed by a subject person for observation (examination) until natural excretion from the living body of the subject, is propelled within the interior of the internal organs such as stomach or small intestine by peristaltic motion of such organs, and takes images of the interior of the organs (inside the body cavity) utilizing the imaging function.

Also, while moving along and observing the organ-interiors, the image data taken by the capsule type endoscope inside the organ are successively transmitted by such a wireless function as radio communication to an external unit or device provided at an outer section of the subject, and such data are stored in a memory provided for the external device. The subject, by carrying the external device having the radio function and the memory function, will be able to behave without any restriction during the observation time from swallowing of the capsule type endoscope until its excretion. After the observation, a physician or nurse will be able to perform diagnoses by displaying the internal images of the body cavity over a structural component for demonstration, such as a display, based on the image data accumulated in the memory of the external device.

Of this kind of capsule type endoscope, for example, there is a swallowable type of endoscope as shown in the Unexamined Patent Publication No. 2002-345743. In this publication, a constitution is proposed wherein a capsule type endoscope is furnished with a built-in battery or cell for supplying electric power, and a LED emits illumination for lighting by the electric power supplied by the battery, an image sensor detects the reflected images from the body cavity of the subject to collectively acquire the image information, and such image information is radio-transmitted from the transmission circuit.

In the above-mentioned capsule type endoscope, for example, if a frequency of transfer clock of an image sensor does not coincide with the frequency of an image signal read-out clock in a signal processing section, picture quality of the image might occasionally deteriorate. On the other hand, if the frequency of the transfer clock of the image sensor does coincide with that of the image signal read-out clock in the image processing section or the like, the edge of the read-out clock conforms to the image signal from the image sensor. Therefore, at least, no such a problem will be encountered.

Nevertheless, since the clock frequency might sometimes be lowered for reducing the current consumption, it may involve a case that the read-out clock be frequency-divided. In that case, for example, a clock edge sometimes appears in every other picture element, thereby causing the clock edge to disaccord with a picture signal from the image sensor. Also, for generation of the above mentioned clock, a switching control is practiced by employing, for example, FET, hence such operation of FET might cause the current consumption to increase at the clock edge, which is a changing point for the clock. There may be a case that a noise tends to migrate into the current source in response to the increased current consumption, thereby affecting the captured picture image and resulting in a problem of deterioration in the quality of the receiving picture.

The present invention has been made in light of the above-mentioned problems, and makes it objective to at least provide an intra-subject device and the related medical device, which are capable of obtaining a high quality signal with lessened noise because the contaminant noise in the image signal is successfully cancelled.

BRIEF SUMMARY OF THE INVENTION

Accordingly, an intra-subject device is provided for acquiring internal information of a subject to be examined. The intra-subject device comprises an illumination component for emitting an illumination light illuminating an interior of a body cavity of the subject and an image capturing component for acquiring image data of the body cavity interior of the subject illuminated by the above-mentioned illumination component. The intra-subject device is also provided with a parameter memory for recording a parameter to be used for canceling any contaminant noise in color information of the picture image acquired by the above-mentioned image pickup component, and is also provided with a transmission section for transmitting the above-mentioned image data added with a parameter recorded by the parameter memory.

By this constitution, the parameter for canceling the noise pattern contaminating the color information is transmitted in addition to the image data, so that such noise can be effectively cancelled.

Also, when the phase of the above-mentioned noise pattern coincides with that of each color information of the image data acquired by the image pickup component, the above-mentioned parameter can be used to cancel the noise contained in each phase of the each color information of the picture image.

In such a case, since the noise pattern is in-phase with the color information of the image data, the parameter data can be more regular (periodic) and hence the amount of information can be lessened.

Also, in the case where the above-mentioned clock for acquiring the image data is frequency-divided, the above-mentioned intra-subject device can be further provided with a clock-generation section for generating an odd-number clock for picture elements for each scan line of the color information of the image data.

Hence, the device can be advantageous for canceling the noise.

Also provided is a medical device comprising an intra-subject unit, to be internally positioned into a body of a subject to be examined, for acquiring information on an interior of the subject, and a signal receiving unit configured to be arranged outside the subject and capable of receiving the signals transmitted from the above-mentioned intra-subject unit.

In this case, the receiver unit can be provided with a receiving section for receiving signals transmitted from the afore-mentioned radio transmitting means, and with a cancel section for canceling contaminant noises in the color information of the afore-mentioned image data based on the parameter information on the afore-mentioned noise pattern added to the image data received at the above-mentioned receiving section.

Further, by controlling the motions of the above-mentioned illumination component and the image pickup component, black image data can be acquired. So doing, since the black image data might contain therein noise elements, the canceling can be effected by use of such noise information contained in the black image data.

The intra-subject device or the medical device thereof are able to obtain low-noise excellent image signals, because any contaminant noise in the image signals can be cancelled by canceling contaminant noise in color information of the image, based on the parameter value of the above-mentioned noise pattern, if image data obtained by the image pickup component is contaminated with noise at each color information.

BRIEF DESCRIPTION OF THE DRAWINGS

These and other features, aspects and advantages of the apparatus and methods of the present invention will become better understood with regard to the following description, appended claims, and accompanying drawings, where:

DETAILED DESCRIPTION OF THE PREFERRED EMBODIMENTS

Embodiments of the invention will be described hereinbelow with reference to the accompanying drawings.

Further, it should be noted that the present invention is not limited to these embodiments, but variously modified embodiments will occur to persons skilled in the art without departing from the substance of the present invention.

Figure 1:
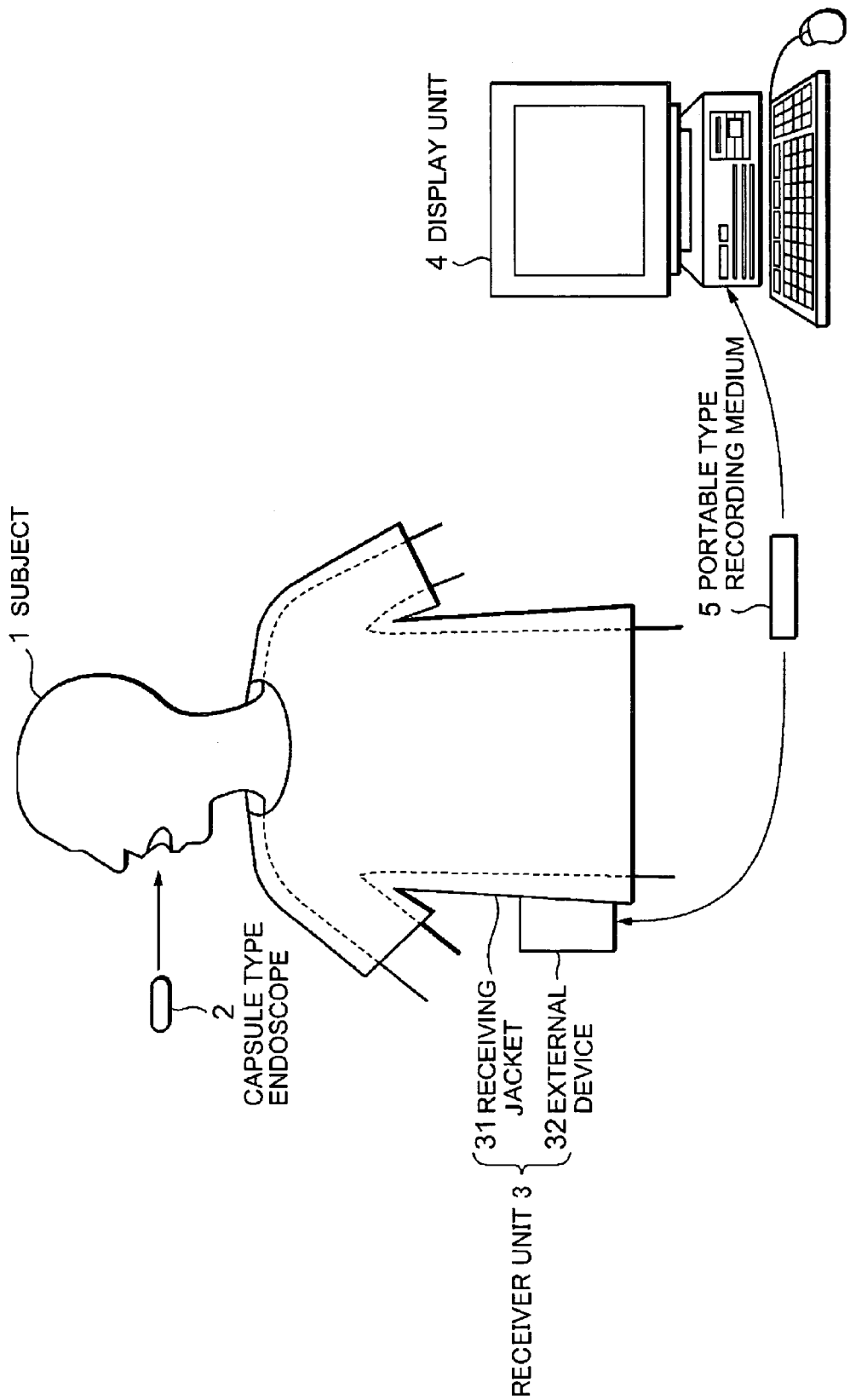
FIG. 1 is a schematic diagram showing an overall configuration and arrangement of a wireless type intra-subject information collecting system including the intra-subject device according to an embodiment of the present invention.

FIG. 1 is a schematic diagram showing an overall constitution of a wireless type intra-subject information collecting system including an intra-subject device according to a first embodiment. In the wireless type intra-subject information collecting system, a capsule type endoscope is explained below, as an example of the intra-subject device.

In FIG. 1, the wireless type intra-subject information collecting system is provided with a receiver unit 3 having a radio receiving function, and a capsule type endoscope 2 (an intra-subject device) which is internally placed or loaded in a subject 1 to perform capturing of coelomic images of the subject 1 and transmitting data including the image signals to the receiver unit 3. Further, the wireless type intra-subject information collecting system is provided with a display unit 4 for displaying the coelomic picture images, based on the image signals received by the receiver unit 3, and a portable type recording medium 5 for delivery of the data between the receiver unit 3 and the display unit 4. The receiver unit 3 is provided with a receiving jacket 31 to be worn by the subject 1, and an external device 32 for processing the radio-signals upon being received. It should be noted that the capsule type endoscope 2 and the receiver unit 3 are both included in the medical device.

The display unit 4 is provided for displaying the bodycavity picture images as captured by the capsule type endoscope 2, and has such a constitution as a workstation to display picture images based on the data acquired from the portable type recording medium 5. More specifically, the display unit 4 may be constituted so as to directly display picture images by means of a CRT display or a liquid-crystal display or may otherwise be constituted as a printer or the like, capable of outputting the picture images to other media.

The portable type recording medium 5 is formed to be detachably connected to the external device 32 and to the display unit 4, and is constituted to be able to output or record the data when connected to the respective device and unit. In this embodiment, the portable recording medium 5 is connected to the external device 32 to record the data transmitted from the capsule type endoscope 2, while the latter traverses the body cavity of the subject 1. After the capsule type endoscope 2 is excreted out of the subject 1, or after completion of the internal imaging of the subject 1, the portable recording medium 5 is detached from the external device 32 and is connected to the display unit 4, thereby allowing the display unit 4 to read out the data recorded on the portable recording medium 5. When the delivery of the data between the external device 32 and the display unit 4 is executed, for example, by a mobile type recording medium such as a Compact-Flash memory, the subject 1 is allowed to move around more freely than the case of a direct wiring connection made between the external device 32 and the display unit 4, while the coelomic image data is being collected. Although the data delivery between the external device 32 and the display device 4 is herein made by means of the portable recording medium 5, this invention is not limited to such method. For example, a built-in recording medium such as a hard disk may be incorporated in the external device 32, and either a wiring connection or a wireless connection may be provided between the external device 32 and the display device 4 for the data transmittal therebetween.

Figure 2:
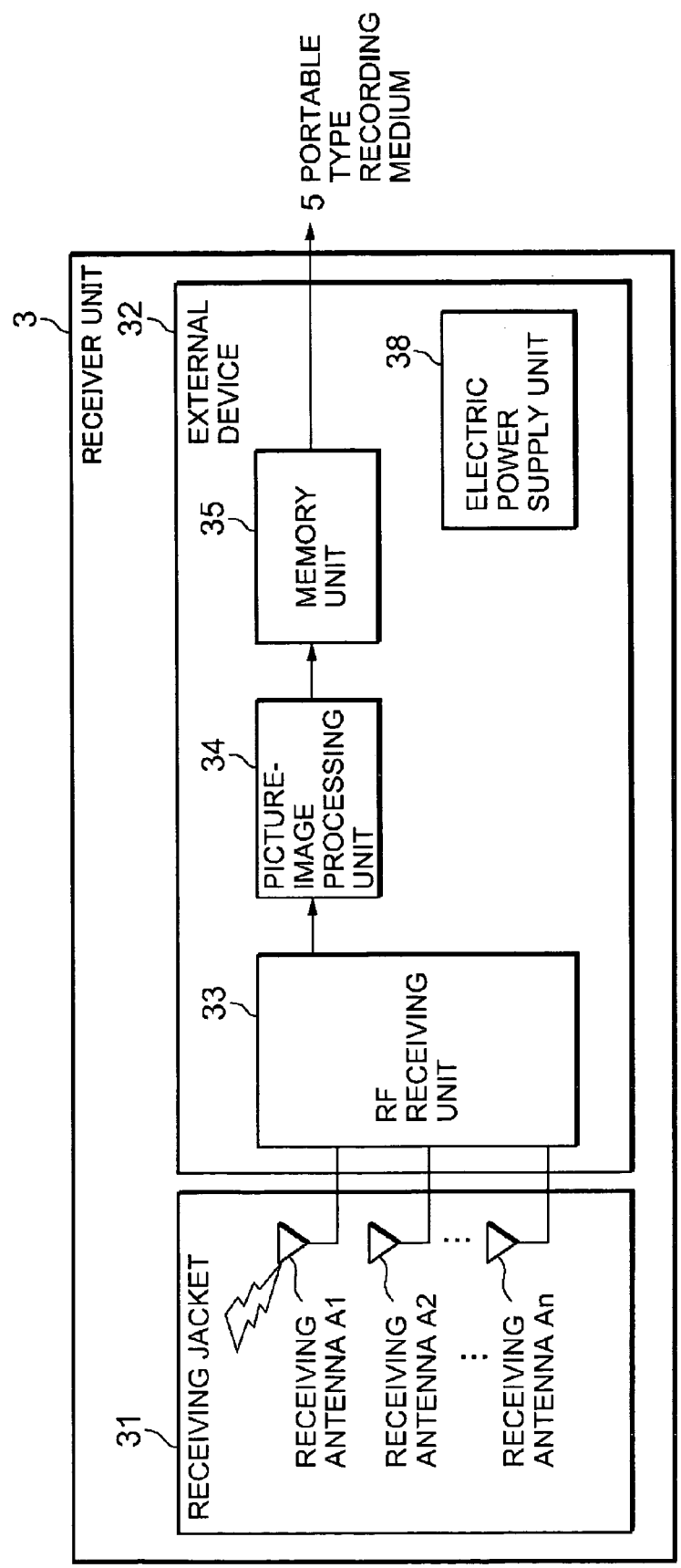
FIG. 2 is a block diagram showing an internal constitution of the receiver unit of the embodiment of FIG. 1.

Now, an explanation of the constitution of the receiver unit 3 will be provided hereinbelow with reference to the block diagram of FIG. 2. The receiver unit 3 has a function of receiving the image data of the interior of a subject, i.e., intra-subject image data when such data is radio-transmitted from the capsule type endoscope 2. As shown in FIG. 2, the receiver unit 3 has such a shape that the subject 1 may wear on his body, and is further provided with a receiving jacket 31 equipped with antennas A1 to An, and an external device 32 for processing the radio-signals received via receiving jacket 31. The receiving antennas A1 to An may not necessarily be directly mounted on the receiving jacket 31. For example, the receiving antennas A1 to An may be directly attached to the external surface of the subject to be examined, and may also be formed as detachable such that it is capable of being detachably provided on the receiving jacket 31.

The external device 32 includes a RF receiving unit 33, an image processing unit 34 and a memory unit 35. The RF receiving unit 33 executes an operation of predetermined signal processing such as demodulation of the radio-signals received by the receiving antennas A1 to An, to extract image data acquired by the capsule type endoscope 2 from radio-transmitted signals. The image processing unit 34 performs a necessary image processing on the extracted image data. The memory unit 35 records the image data that have been processed by the image processing operation. The external device 32 processes the radio-signals transmitted from the capsule type endoscope 2. In this embodiment, the image data is recorded in the portable type recording medium 5 through the memory unit 35. The external device 32 is equipped with a power supply unit 38, which is either a designated battery or an AC source adaptor, and the respective constituents of the external device 32 are supplied with electrical power from the power supply unit 38 as driving energy.

Figure 3:
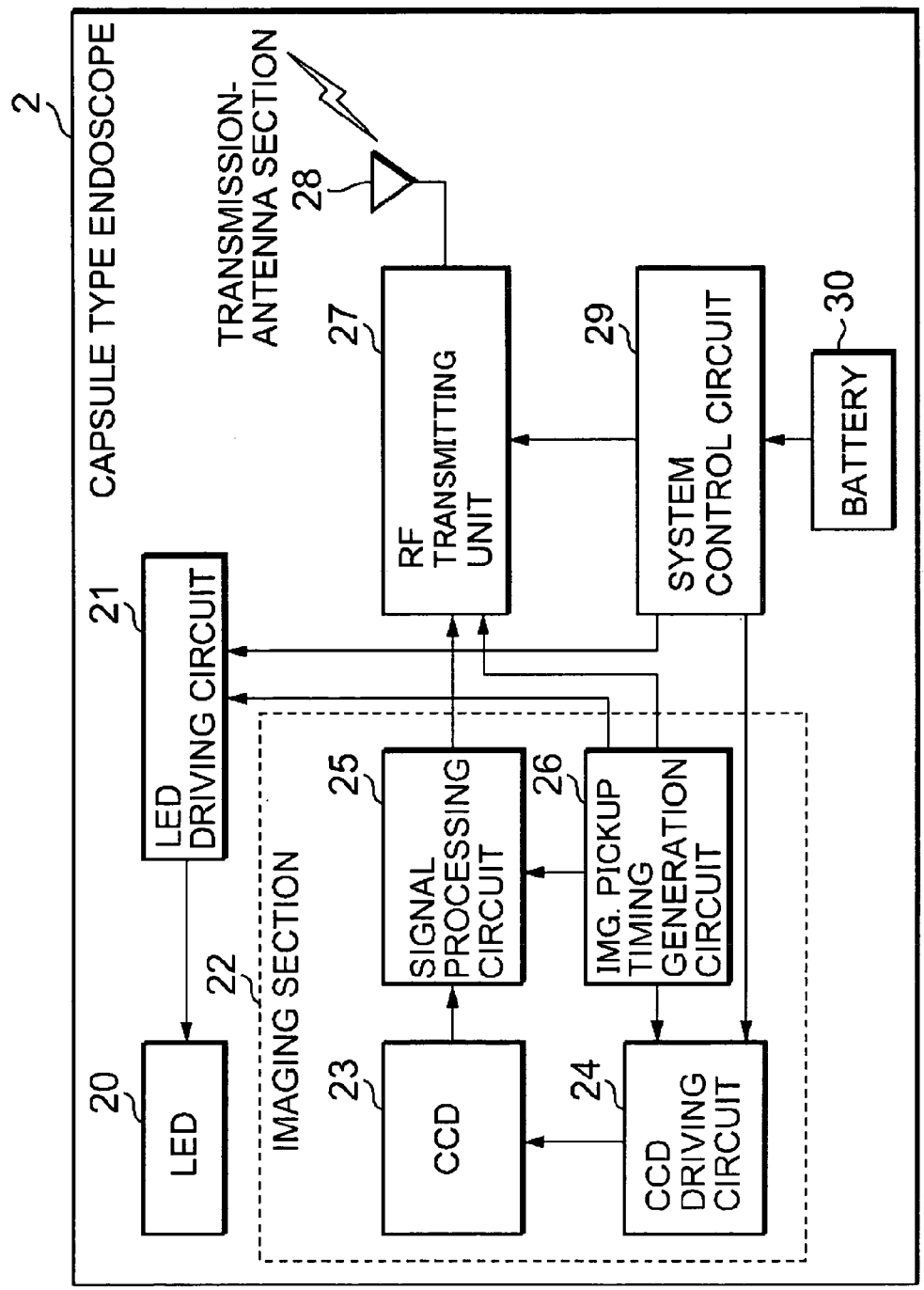
FIG. 3 is a block diagram showing an internal constitution of the capsule type endoscope of the embodiment of FIG. 1.

Now, a description of the constitution of the capsule type endoscope will be provided hereunder, with reference to the block diagram of FIG. 3.

As shown in the block diagram in FIG. 3, the capsule type endoscope 2 is provided with a light-emitting diode (LED) 20, a LED driving circuit 21, a charge coupled device (CCD) 23, a CCD driving circuit 24, a signal-processing circuit 25 and an image pickup timing generation circuit 26. The LED 20 is an illuminating or lighting member for illuminating, for example, an examined site in the body cavity of the subject 1. The LED driving circuit 21 controls the driving condition of the LED 20. The CCD 23 is an imaging member to capture the images of light reflecting from the illuminated area inside the body cavity. The CCD driving circuit 24 controls a driving condition of the CCD 23. The signal-processing circuit 25 processes the image-signals output from the CCD 23 into a desired type of image data. The image pickup timing generation circuit 26 is a clock generation section to output reference clocks for providing drive-timing such as a lighting timing of the LED 20 or an imaging timing of the CCD 23. The capsule type endoscope 2 is provided with a RF transmitting unit 27 for modulating a picked-up image data into RF signals, and with a transmission-antenna section 28 as a radio-transmitting portion for radio-transmitting the RF signals output from the RF transmitting unit 27. The capsule type endoscope 2 is further provided with a system control circuit 29 for controlling the operation of the LED driving circuit 21, the CCD driving circuit 24 and the RF transmitting unit. The CCD 23, the CCD driving circuit 24, the signal processing circuit 25 and the imaging timing generation circuit 26 as a whole are referred to as an imaging section 22. Owing to provision of the above constitution, the capsule type endoscope 2 operates for capturing and collecting, by means of the CCD 23, the image signals of the examined site illuminated by the LED 20, based on the reference clocks constituting desired imaging timings, while the capsule type endoscope 2 is within the subject 1. The captured analog image signals are processed by the signal processing circuit 25 based on the reference clocks, and are further modulated by the RF transmitting unit 27 into RF signals which are in turn transmitted to the exterior of the subject 1 through the transmission-antenna section 28.

That is to say, the image pickup timing generation circuit 26 outputs the reference clocks constituting the drive-timings to the LED driving circuit 21, the CCD driving circuit 24, and the signal processing circuit 25.

Figure 4:
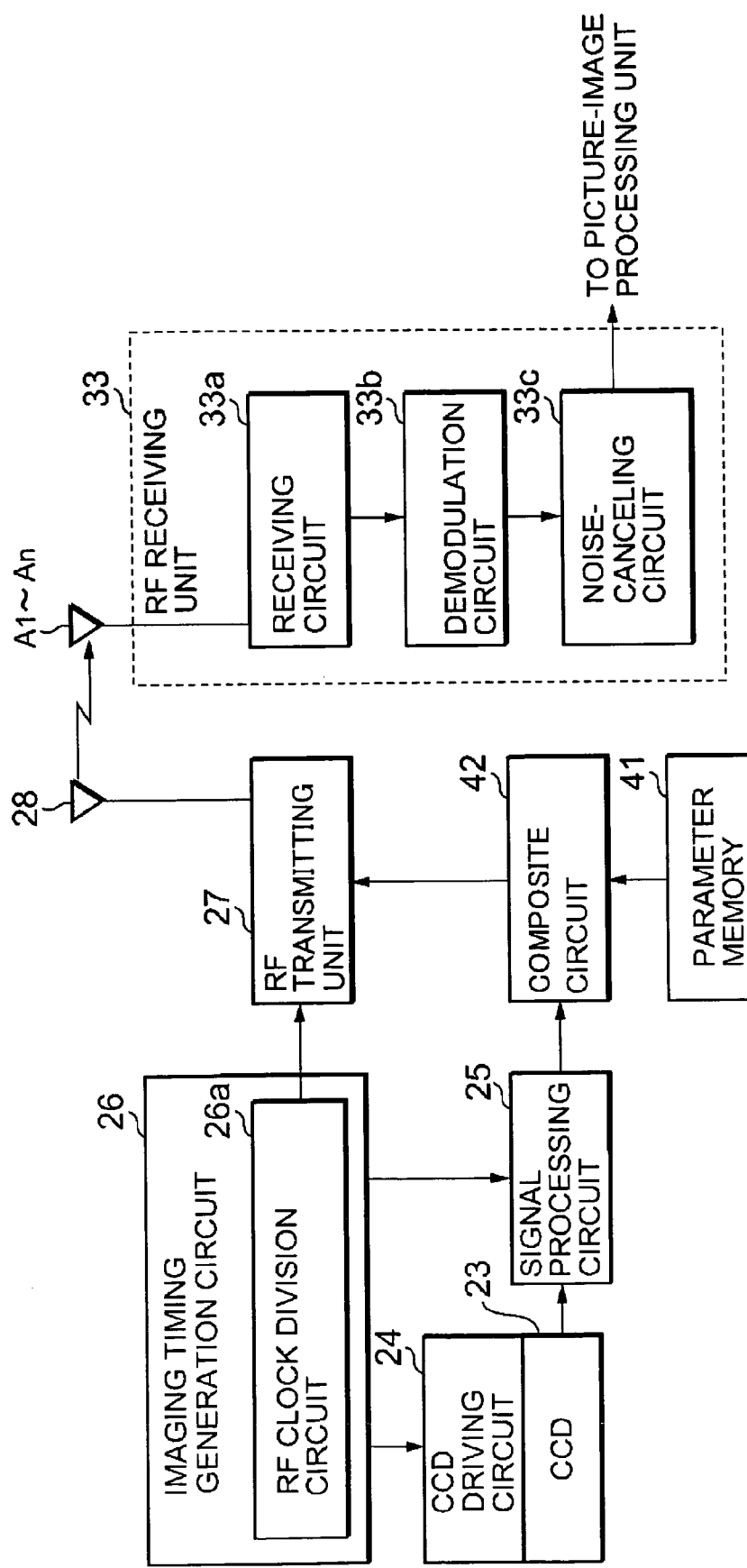
FIG. 4 is a block diagram showing an example of the configuration and arrangement of the major section of the medical device of FIG. 1.

As best shown in the block diagram of FIG. 4, the imaging timing generation circuit 26 is also provided with a RF-use clock dividing circuit 26a functioning as a frequency-dividing section for frequency-dividing the reference clocks, and outputs the clocks being divided from the RF-use clock dividing circuit 26a to the RF transmitting unit 27. The RF-use reference clocks output from the imaging timing generation circuit 26 are generated to be higher accuracy than the reference clocks generated in the RF transmitting unit 27, so that the absolute value of frequency drift is set small. Therefore, upon outputting the RF-use reference clocks, the above-mentioned highly accurate reference clocks constituting the CCD imaging timing are frequency-divided by the RF-use clock dividing circuit 26a, thereby being formed in such RF-use reference clocks to be used for providing phase-lock for the reference clocks of the RF. Namely, by outputting the RF-use reference clocks to the RF transmitting unit 27, it is possible for the transmission carrier wave to have a stable oscillation.

Figure 5:
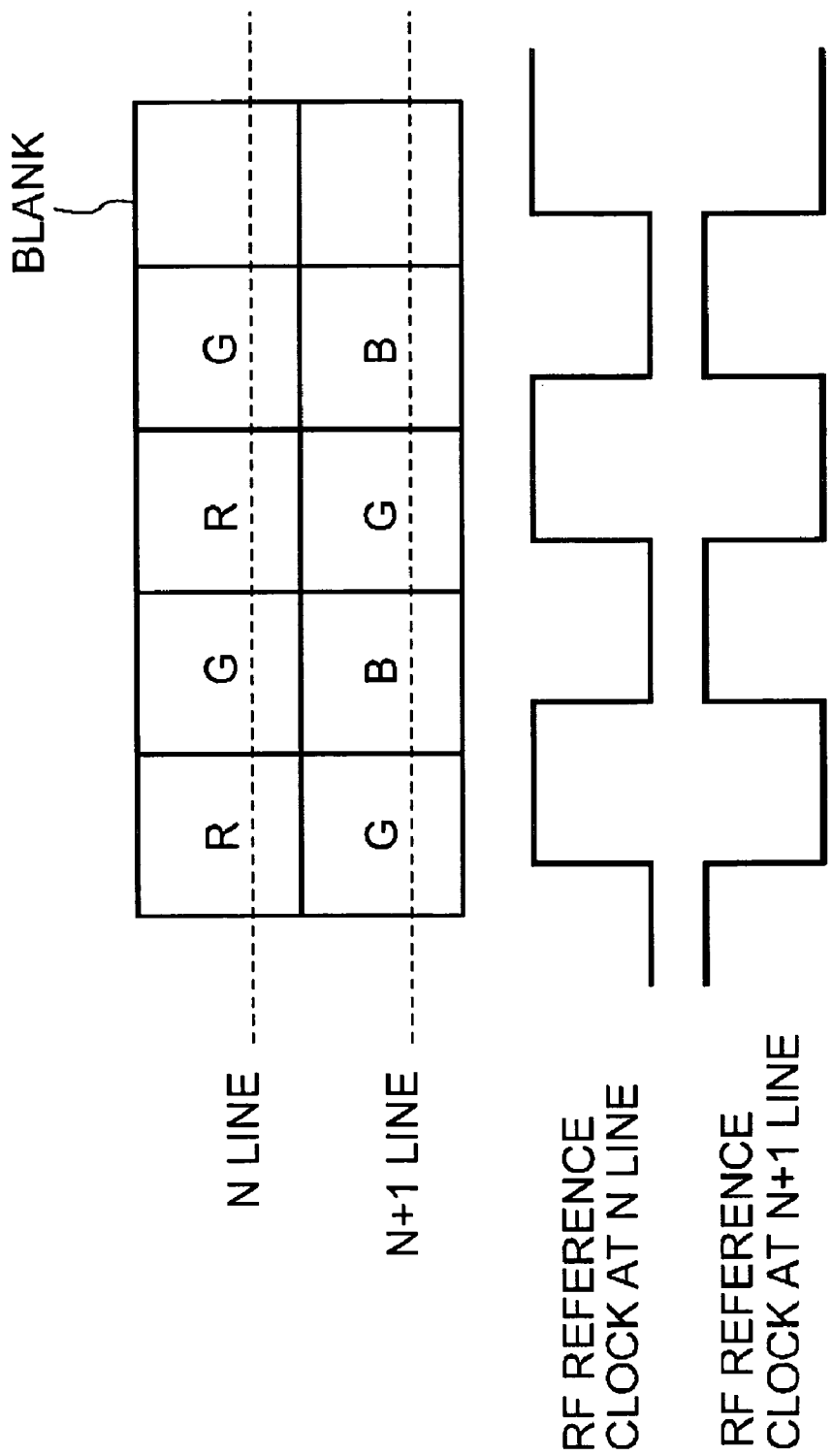
FIG. 5 is an explanatory diagram showing the relationship between the line-array in the picture-element color information and the RF reference clock.

Now, provided hereunder is an explanatory description of a case where the RF reference clocks generated by the imaging timing generation circuit 26 are applied to a Bayer array CCD 23. For example, as shown in the diagram of FIG. 5 indicating the relationship between the line arrays and the RF reference clocks, in the case of the Bayer array, N line is constituted by red R picture elements and green G picture elements which are alternately disposed as color information, and N+1 line is constituted by green G picture elements and blue B picture elements which are alternately disposed as color information. In such a constitution, for example, if the RF-use reference clocks are generated by dividing the image reference clocks to have a half frequency, without providing any specific setting, a clock edge appears in every other picture element. In addition, if the RF-use reference clocks to be supplied to the RF transmitting unit 27 are output from the imaging section 22 as clocks, a fluctuation of power supply voltage is generated at the clock edges. Hence, as will be understood from the foregoing description, captured picture images are contaminated with noise, so that the images are adversely affected.

Therefore, in the present embodiment, for example, in case where frequency divided RF-use reference clocks having a half frequency of the imaging reference clocks are generated by means of the imaging timing generation circuit 26, the number of 1-line picture element clocks is set for an odd number. That is to say, in the Bayer array, usually on N line (an odd-numbered line for example), color information of red R and green G is constituted by four (even-numbered) picture-element clocks, and on N+1 line (an even-numbered line for example), color information of green G and blue B is constituted by four (even-numbered) picture-element clocks. In this embodiment, a blank area is set for every fifth position of each line. Further, in case of the odd-numbered line, the RF-use reference clocks from the imaging timing generation circuit 26 start to edge up at the red R, start to edge down at the green G, and starts to edge up again at the blank. In case of the subsequent even-numbered line, the RF-use reference clocks are generated so as to edge down at the green G, edge up at the blue B and edge down again at the blank. Namely, provision of the blank areas for the respective lines allows the RF-use reference clocks to set for edging up at picture elements of the red R and the blue B, and for edging down at picture element of the green G on all of the lines, by means of a single kind of the RF-use reference clock generated at the imaging timing generation circuit 26.

In FIG. 4, the capsule type endoscope 2 according to the present embodiment is provided with the imaging timing generation circuit 26, the parameter memory 41 and the composite circuit 42.

The imaging timing generation circuit 26 allocates the setting for the edging-up and the edging-down to each of the color-information shown in FIG. 5. The parameter memory 41 stores therein parameter values for canceling the contaminant noise in the color-information. The composite circuit 42 adds the parameter values from the parameter memory 41 to the image-information input from the signal processing circuit 25 to the circuit 42, at the time of transmitting the image-information.

The imaging timing generation circuit 26 allocates the setting for the edging-up and the edging-down to each of the color-information. In the present embodiment, the phenomenon, that a specific noise pattern is entrapped in the imaging signal along with change in the current consumption at each signal edge, is used. Since it is supposed that a noise pattern entrapped in each color-information might alter with, for example, different capsule type endoscopes, it is preferable to preliminarily measure the respective noise patterns by means of a suitable measuring instrument. The imaging timing generation circuit 26 outputs the imaging reference clocks to the CCD driving circuit 24, and the CCD 23 outputs the analog image signals at the timing of the RF-use reference clocks, hence the image signals are output as digital image-information at the signal processing circuit 25. The parameter value stored in the parameter memory 41 is the parameter value of the noise component, which has been derived from preliminary measurement of the noise pattern entrapped in each color-information as described beforehand. The RF transmitting unit 27 uptakes the image-information added with the parameter value at the timing of the RF-use reference clocks input from the RF clock dividing circuit 26a and transmits, in a frame configuration, to the exterior of the subject via the transmission-antenna section 28.

Further, the RF receiving unit 33 is provided with a receiving circuit 33a, a demodulation circuit 33b and a noise-canceling circuit 33c. The receiving circuit 33a is a receiving section to receive and amplify the radio signals from receiving antenna A1 to An, to which selective controls have been previously applied according to the reception field intensity. The demodulation circuit 33b demodulates the radio signals. The noise-canceling circuit 33c is a canceling section for canceling the noise in the image information, based on the parameter values added to the image information. The noise-canceling circuit 33c extracts the parameter values from a received frame, and stores those in a parameter memory, and at the same time, cancels the noise entrapped in each color-information based on the parameter values. For example, the noise cancellation on each color-information is performed by changing the offset values of signals based on the parameter values.

In the present embodiment, parameter values of uniform noise component, which is entrapped in each color-information of the image data, are measured beforehand, and such parameter values are added to the image-data and then transmitted to the receiving unit. Then, at the side of the receiving unit, the noise entrapped in each color-information is cancelled by using the parameter values. Therefore, the noise entrapped in the image signals can readily be cancelled, and high quality image signals with lessened noise can be acquired.

Also, in this embodiment, for the purpose of reducing the load of the capsule type endoscope, the noise-canceling operation is arranged to be conducted on the receiving unit side. However, in the case where the processing capacity of the capsule type endoscope is sufficiently high, it is also possible to have the noise-canceling operation done within the capsule type endoscope. In such a case, the noise entrapped in the analog image signal can be easily cancelled, using the above-mentioned parameter values of noise components, for example, at the signal processing circuit 25.

Further, in the present embodiment, assuming that the noise parameter values vary along with each piece of the capsule type endoscope, the measured parameter values are transmitted to the receiving unit side. However, since it is also possible that the parameter values may be almost uniform, despite individually different pieces of the capsule type endoscopes involved, then in such a case, it is also possible to have such parameter values stored in advance by a parameter memory provided at the receiving unit side, without transmitting the parameter values. Also, for the RF-use reference clocks generated from the imaging timing generation circuit 26, a clock commonly applicable to the whole lines may be used. However, it is also possible to generate clocks respectively for the even-numbered lines and for the odd-numbered lines, with the phase thereof shifted by 90 degree, and may use these clocks by switching over in accordance with the applied line.

Figure 6:
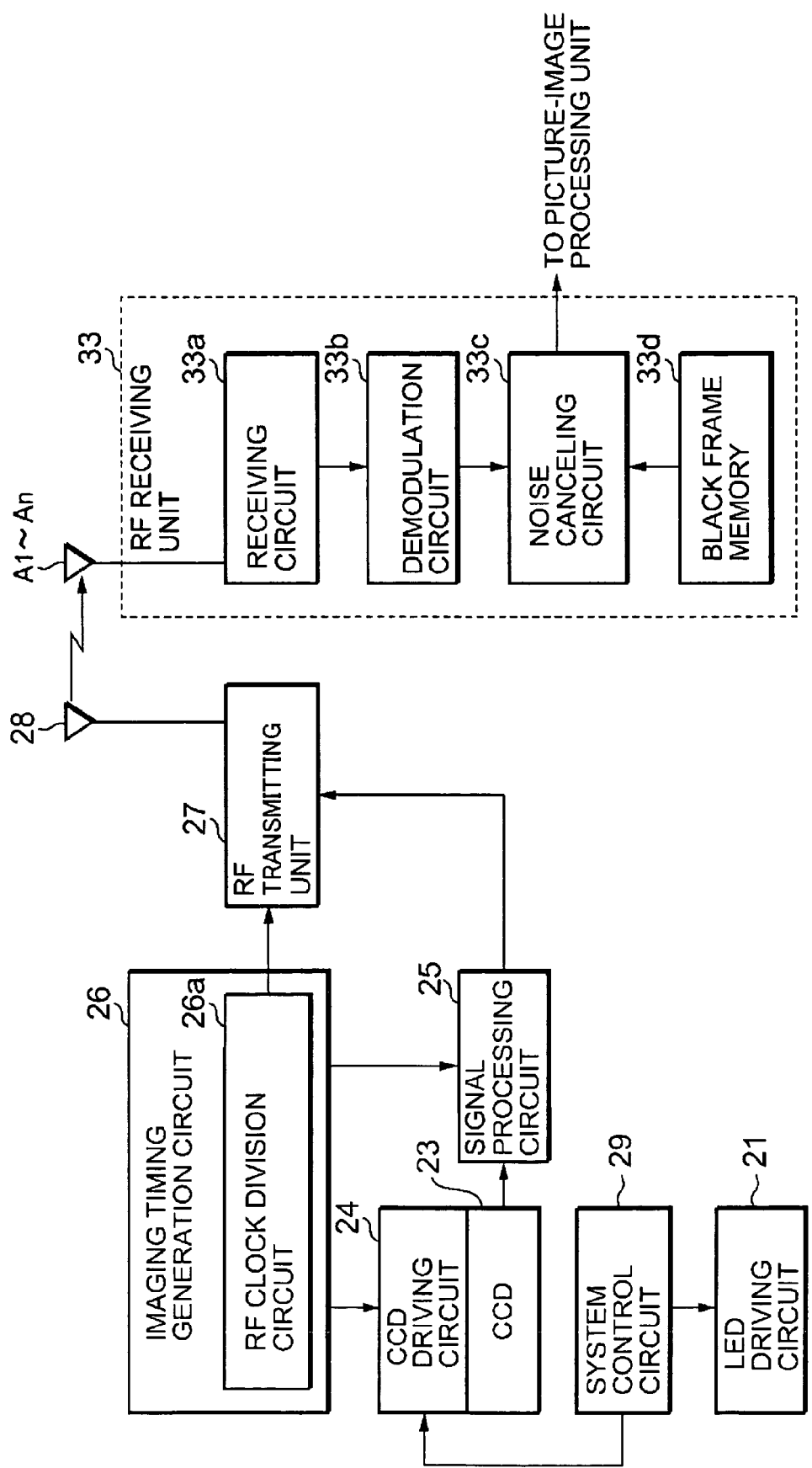
FIG. 6 is a block diagram showing the configuration and arrangement of the major section of an medical device according to another embodiment.

FIG. 6 is a block diagram showing another embodiment of a medical device according to the present invention. A difference of this embodiment from the previous embodiment resides in that black image-information is acquired by controlling the operation of the LED driving circuit 21 and the CCD driving circuit 24 using the system control circuit 29 as an operational control section, such that black image-information is made into a frame constitution (hereafter referred to as "the black frame") and is transmitted together with other image-information in the frame constitution (hereafter referred to as "the image frame") from the RF transmitting unit 27, and that the noise in the image-information is cancelled by the noise canceling circuit 33c, based on the black image-information from a black frame memory 33d provided in the RF receiving unit 33 for storing the received black image-information.

Figure 7:
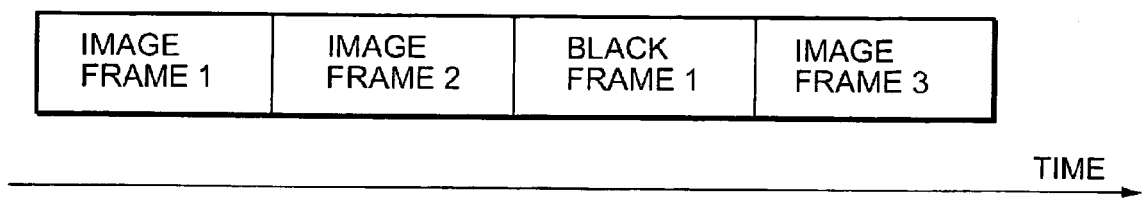
FIG. 7 is a schematic diagram showing an outline scheme of the frame being transmitted by the medical device of FIG. 6.

That is to say, the system control circuit 29 controls operation of the LED driving circuit 21 and the CCD driving circuit 24, acquires black image signals within a subject by the CCD 23 while the LED is turned off, and allows the signal processing circuit 25 to output the black image signals. The black image signals, containing noise components, are processed by the signal processing circuit 25, in the same way as ordinal image signals, and converted to RF signals in the frame constitution (the black frame) to be transmitted to the exterior of the subject through the transmission-antenna section 28. Also, the system control circuit 29 controls operation of the LED driving circuit 21 and the CCD driving circuit 24, so as to acquire a frame of black image information in a plurality of the ordinary image information. FIG. 7 illustrates an example of the frame constitution.

The RF receiving unit 33, similar to that of the previous embodiment, receives and amplifies, with the receiving circuit 33a, the radio signals received at the receiving antennas A1 to An, selectively controlled according to the electric field intensity, and also demodulates the radio signals with the demodulation circuit 33b. In succession, the noise canceling circuit 33c cancels noise in the received image-information, based on the black image information containing a noise component and stored in the black frame memory 33d. The black image information of the black frame memory 33d is rewritten to the latest black image information whenever a black frame is received.

Thus, in the present embodiment, the black image information containing therein a noise component with respect to the interior of the subject is obtained through the operation control of the LED and the CCD, and based on such a black image-information, the noise component contained in the ordinal image signals is cancelled. Therefore, noise entrapped in the image information can be readily cancelled, so that high quality image signals with lessened noise can be acquired.

While there has been shown and described what are considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

The invention claimed is:

1. An intra-subject device adapted for being introduced into an interior of a subject for acquiring information of the interior of the subject, the intra-subject device comprising:
   a lighting member for outputting an illuminating light for illuminating the interior of the subject;
   an imaging member for acquiring image-information of the interior of the subject illuminated by the lighting member;
   a parameter memory that records a parameter, the parameter comprises parameter information of a noise pattern generated when acquiring the image information by the imaging member and contained in color information of the image information acquired by the imaging member and configured to be used to cancel the noise pattern contained in the color information of the image, the noise pattern being derived from preliminary measurement of noise pattern entrapped in color information;
   a composite circuit configured to add the parameter from the parameter memory to the image-information; and
   a transmitting section for transmitting the image information added with the parameter recorded in the parameter memory.

2. The intra-subject device according to claim 1, wherein when the pattern of the noise pattern is in-phase with each color information of the image information, the parameter is used to cancel the noise pattern of the same phase contained in the each color information of the image information based on the parameter information of the noise pattern.

3. The intra-subject device according to claim 1, wherein the intra-subject device further comprises a clock generation section for generating an odd-numbered picture-clement clock to each line of the color information of the image, when the clock to be used for acquiring the image information is frequency-divided.

4. A medical device comprising:
   an intra-subject device to be introduced into an interior of a subject for acquiring information of the interior of the subject; and
   a receiving device configured to be capable of receiving, outside the subject, radio-signals transmitted from the intra-subject device;
   wherein the intra-subject device comprises:
   a lighting member for outputting illuminating light to illuminate the interior of the subject;
   an imaging member for acquiring image information of the interior of the subject illuminated by the lighting member; and
   a transmitting section for transmitting the image information acquired by the imaging member added with parameter information of a noise pattern generated when acquiring the image information by the imaging member and contained in color information of the image information acquired by the imaging member; and
   wherein the receiving device comprises:
   a receiving section for receiving signals transmitted from the transmitting section; and
   a canceling section for at least partially canceling the noise pattern contained in the color information of the image information based on the parameter information of the noise pattern added to the image information received by the receiving section, the noise pattern being derived from preliminary measurement of noise pattern entrapped in color information.

5. The medical device according to claim 4, wherein when the parameter of The noise pattern is in-phase with each color information of the image information, the parameter is used to cancel The noise pattern of the same phase contained in the each color information of the image information, based on the parameter information of the noise.

6. The medical device according to claim 4, further comprising a clock generation section for generating an odd-numbered picture-image clock to each line of the color information of the image, when the clock for acquiring the image data is frequency-divided.

7. A medical device including an intra-subject device adapted for being introduced into an interior of a subject for acquiring information of the subject and a receiving device configured to be capable of receiving signals transmitted from the intra-subject device at an exterior of the subject, wherein the medical device comprises:
   a lighting member for outputting an illuminating light for illuminating the interior of the subject;
   an imaging member for acquiring image information of the interior of the subject illuminated by the lighting member;
   an operation controlling section for controlling the operation of the lighting member and imaging member such that the imaging member acquires image information while the lighting member is not outputting the illuminating light to acquire black image information; and
   a transmitting section for transmitting the image information and the black image information acquired by the imaging member;
   and wherein the receiving device comprises:
   a receiving section for receiving signals transmitted from the transmitting section; and
   a canceling section for canceling at least a portion of noise in the received image information generated when acquiring the image information by the imaging member and based on noise components contained in the black image information received by the receiving section.

8. The medical device according to claim 7, wherein the transmitting section transmits at least one frame of the black image information.

9. An intra-subject device adapted for being introduced into an interior of a subject for acquiring information of the interior of the subject, the intra-subject device comprising:
   a lighting member for outputting an illuminating light for illuminating the interior of the subject;
   an imaging member for acquiring imaging information of the interior of the subject illuminated by the lighting member;
   a parameter memory that records a parameter, the parameter comprises parameter information of a noise pattern generated when acquiring the image information by the imaging member and contained in color information of the image information acquired by the imaging member, the noise pattern being derived from preliminary measurement of noise pattern entrapped in color information and configured to be used for canceling at least a portion of the noise pattern contained in the color information of the image; and a signal processing circuit that cancels the noise based on the parameter value.

* * * * *